United States Patent [19]

Shiba

[11] Patent Number: 6,063,595

[45] Date of Patent: May 16, 2000

[54] METHOD OF FORMING A MACROMOLECULAR MICROGENE POLYMER

[75] Inventor: Kiyotaka Shiba, Tokyo, Japan

[73] Assignee: Japan Science and Technology Corporation, Kawaguchi, Japan

[21] Appl. No.: 08/871,809

[22] Filed: Jun. 9, 1997

[30] Foreign Application Priority Data

Jun. 10, 1996 [JP] Japan .................................. 8-147184

[51] Int. Cl.⁷ .............................. C12P 21/06; C12P 19/34
[52] U.S. Cl. ...................... 435/69.1; 435/91.1; 435/91.2; 435/91.5
[58] Field of Search ................................. 435/91.1, 91.2, 435/91.5, 69.1; 536/22.1, 23.1

[56] References Cited

U.S. PATENT DOCUMENTS 5,587,287  12/1996  Scalice .......................................... 435/6
5,683,872  11/1997  Rudert .......................................... 435/6

OTHER PUBLICATIONS

Shiba et al (1997). Creation of libraries with long ORFs by polymerization of a microgene. Proc. Natl. Acad. Sci. USA 94: 3805–3810, Apr. 1997.

*Primary Examiner*—Carla J. Myers
*Assistant Examiner*—Diana Johannsen
*Attorney, Agent, or Firm*—Davidson, Davidson & Kappel, LLC

[57] ABSTRACT

A method of forming a macromolecular microgene polymer comprises allowing DNA polymerase to act on oligonucleotides A and B complementary at least partially to each other to effect polymerase chain reaction. According to the present invention, there can be obtained a polymer consisting of a repeating microgene, which is efficiently and simply formed.

5 Claims, 10 Drawing Sheets

794 GACGGTCACCTGCACAAAGGCG
795      AGTTTCCGCACGTCACCTAGGGC

1. Size Marker
2. KY-794 & KY-795

FIG.3

```
         GACGGTCACCTGCACAAAGGCG           KY-794
              AGTTTCCGCACGTCACCTAGGGC     KY-795
```

(pSA32)
GACGGTCACCTGCACAAAGGCGTGCAGTGGATCCCG
GACGGTCACCTGCACAAAGGCGTGCAGTGGATCCCGCGG
GACGGTCACCTGCACAAAGGCGTGCAGTGGATCCCGCCCC
GACGGTCACCTGCACAAAGGCGTGCAGTGGATCCΔΔ
GACGGTCACCTGCACAAAGGCGTGCAGTGGATCCCG

(pYT8)
GACGGTCACCTGCACAAAGGCGTGCAGTAGATCCCGCCCG
GACGGTCACCTGCACAAAGGCGTGCAGTGGATCCCG
GACGGTCACCTGCACAAAGGCGTGCAGTGGATCCCGC
GACGGTCACCTGCACAAAGGCGTGCAGTGGATCCCGCCGG
GACGGTCACCTGCACAAAGGCGTGCAGTGGATCCCΔ
GACGGTCACCTGCACAAAGGCGTGCAGTGGATCCCG
GACGGTCACCTGCACAAAGGCG

(pSA33)
GACGGTCACCTGCACAAAGGCGTGCAGTGGATCCCGGCG
GACGGTCACCTGCACAAAGGCGTGCAGTGGATCCCGT
GACGGTCACCTGCACAAAGGCGTGCAGTGGATCCCGCCA
GACGGTCACCTGCACAAAGGCGTGCAGTGGATCCGCCA
GACGGTCAC

(pYT5)
GACGGTCACCTGCACAAAGGCGTGCAGTGGATCCCGCCGG
GACGGTCACCTGCACAAAGGCGTGCAGTGGATCCCGT
GACGGTCACCTGCACAAAGGCGTGCAGTGGATCCCG
GACGGTCACCTGCACAAAGGCGTGCAGTGGATCCCGCCGG
GACGGTCACCTGCACAAAGGCGTGCAGTGGATCCCΔ
GACGGTCACCTGCACAAAGGCGTGCAGTGGATCCCΔ
GACGGTCACCTGCACAAAGGCGTGCAGTGGATCCCGCCGG
GACGGTCACCTGCACAA

```
794    GACGGTCACCTGCACAAAGGCG
795              AGTTTCCGCACGTCACCTAGGGC

794    GACGGTCACCTGCACAAAGGCG
783               GTTTCCGCACGTCACCTAGGGC
```

1. Size Marker
2. KY-794 & KY-795
3. KY-794 & KY-783

```
794    GACGGTCACCTGCACAAAGGCG
795              AGTTTCCGCACGTCACCTAGGGC

845    GACGGTCACCTGCACAGGCG
846              AGTCCGCACGTCACCTAGGGC
```

1 2 3 4 5

1. Size Marker
2. KY-794 & KY-795   63℃
3. KY-845 & KY-846   63℃
4. KY-794 & KY-795   66℃
5. KY-845 & KY-846   66℃

```
794    GACGGTCACCTGCACAAAGGCG
795                AGTTTCCGCACGTCACCTAGGGC
```

1. Size Marker
2. *Pfu* DNA Polymerase
3. Exo⁻ *Pfu* DNA Polymerase

```
794    GACGGTCACCTGCACAAAGGCG
795                AGTTTCCGCACGTCACCTAGGGC

808    GACGGTCACCTGCAAACGGAGC
809                ATTGCCTCGACGTCACCTAGGGC
```

1. Size Marker
2. KY-794 & KY-795
3. KY-808 & KY-809

FIG. 8

```
794    GACGGTCACCTGCACAAAGGCG
827    CTGGGTCACCTGCACAAAGGCG
828    GACCCACACCTGCACAAAGGCG
829    GACGGTGTGCTGCACAAAGGCG
830    GACGGTCACGACCACAAAGGCG

795              AGTTTCCGCACGTCACCTAGGGC
831              AGTTTCCGCTGCTCACCTAGGGC
832              AGTTTCCGCACGAGTCCTAGGGC
833              AGTTTCCGCACGTCAGGAAGGGC
834              AGTTTCCGCACGTCACCTTCCGC
835              AGTTTCCGCACGTCACCTAGGCG
```

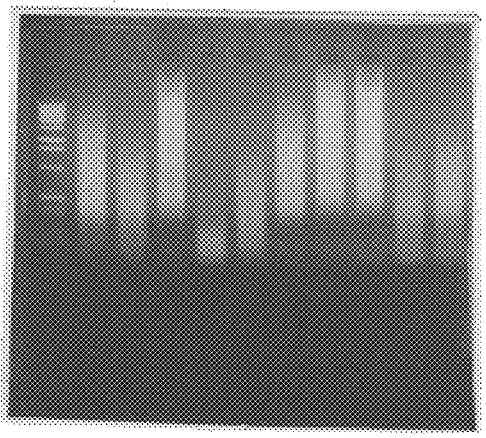

1. Size Marker
2. KY-794 & KY-795
3. KY-827 & KY-795
4. KY-828 & KY-795
5. KY-829 & KY-795
6. KY-830 & KY-795
7. KY-794 & KY-831
8. KY-794 & KY-832
9. KY-794 & KY-833
10. KY-794 & KY-834
11. KY-794 & KY-835

FIG.9

GANGGTCACCNGCACAAAGGCG          KY-812
        AGTTTCCGCACGTCACCTAGGGC    KY-795
(N = A, T, G, C)

(pYT15)
GACGGTCGCCGGCACAAAGGCGTGCAGTGGATCCCG
GACGGTCACCCGCACAAAGGCGTGCAGTGGATCCCG
GACGGTCACCGGCACAAAGGCGTGCAGTGGATCCCG
GACGGTCACCTGCACAAAGGCGTGCAGTGGATCCCG
GATGGTCACCAGCACAAAGGCGTGCAGTGGATCCCA
GACGGTCACCCGCACAAAGGCGTGCAGTGGATCCCG
GACGGTCACCTGCACAAAGGCGTGCAGTGGATCCCA
GACGGTCACCAGCACAAAGGCGTGCAGTGGATCCCG
GACGGTCACCTGCACAAAGGCGTGCAGG (pYT16)
GACGGTCACCTGCACAAAGGCGTGCAGTGGATCCCG
GACGGTCACCTGCACAAAGGCGTGCAGTGGATCCCG
GACGGTCACCAGCACAAAGGCGTGCAGTGGATCCCA
GACGGTCACCCGCACAAAGGCGTGCAGTGGATCCCG
GATGGTCACCGGCACAAAGGCGTGCAGTGGATCCCA
GACGGTCACCTGCACAAAGGCGTGCAGTGGATCCCG<u>CGT</u>
GAGGGTCACCTGCACAAAGGCGTGCAGTGGATCCCA
GACGGTCACCTGCACAAAGGCGTGCAGTGGATCCCA
GACGGTCACCTGCACAAAGGCGTGCAGTGGATCCCG<u>CCGG</u>
GACGGTCACCTGCACAAAGGCGTGCAGTGGATCCCG
GACGGTCACCGGCACAAAGGCGTGCAGTGGATCCCG
GACGGTCAC (pYT20)
    GGTCACCGGCACAAAGGCGTGCAGTGGATCCCG<u>CCGG</u>
GACGGTCACCTGCACAAAGGCGTGCAGTGGATCCCG<u>CCGG</u>
GACGGTCACCTGCACAAAGGCGTGCAGTGGATCCCG
GACGGTCACCTGCACAAAGGCGTGCAGTGGATCCCG<u>CCGG</u>

GACGGTCACCTGCACAAAGGCGTGCAGTGGATCCCG
GACGGTCACCTGCACAAAGGCGTGCAGTGGATCCCG
GACGGTCACCTGCACAAAGGCGTGCAGTGGATCCCA
GACGGTCACCAGCACAAAGGCGTGCAGTGGATCCCA
GAAGGTCACCCGCACAAAGGCGTGCAGTGGATCCCG
GACGGTCACCGGCACAAAGGCGTGCAGTGGATCCCA
GACGGTCACCTGCACAAAGGCGTGCAGTGGATCCCA
GACGGTCACCGGCACAAAGGCGTGCAGTGGATCCCG<u>CCGG</u>
GAAGGTCACCTGCACAAAGGCGTGCAGTGGATCCCG
GACGGTCACCGGCACAAAGGCGTGCAGTGGATCCCG
GAAGGTCACCGGCACAAAGGCGTGCAGTGGATCCCA
GACGGTCACCAGCACAAAGGCGTGCAGTGGATCCCG
GACGGTCACCGGCACAAAGGCGTGCAGTGGATCCCG
GACGGTCACCTGCACAAAGGCGTGCAGTGGATCCCA
GACGGTCACCCGCACAAAGGCGTGCAGTGGATCCCG<u>CCGG</u>
GATGGTCACCGGCAC (pYT22)
GAGGGTCACCCGCACAAAGGCGTGCACTGGATCCCG<u>CCGG</u>
GACGGTCACCTGCACAAAGGCGTGCATTGGATCCCG<u>CCGG</u>
GACGGTCACCGGCACAAAGGGGTGCAGTGGATCCCG
GACGGTCACCTGCACAAAGGCGTGCAGTGGATCCCG<u>CCGG</u>
GACGGTCACCGGCACAAAGGCGTGCAGTGGATCCCA
GATGGTCACCCGCACAAAGGCGTGCAGTGGATCCCA
GATGGTCACCCGCACAAAGGCGTGCAGTGGATCCCG<u>CCGG</u>
GACGGTCACCTGCACAAAGGCGTGCAGTGGATCCCA
GACGGTCACCTGCACAAAGGCGTGCAGTGGATCCCG
GAAGGTCACCGGCACAAAGGCGTGCAGTGGATCCCG

1. Molecular Weight Marker
2. pTZ19R/BL21(DE3)
3. pYT32/BL21(DE3)
4. pYT33/BL21(DE3)

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:1:

```
GACGGTCACC TGCACAAAGG CG                                                  22
```

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:2:

```
CGGGATCCAC TGCACGCCTT TGA                                                 23
```

(2) INFORMATION FOR SEQ ID NO:3:

(i) SEQUENCE CHARACTERISTICS:
      (A) LENGTH: 185 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:3:

```
GACGGTCACC TGCACAAAGG CGTGCAGTGG ATCCCGGACG GTCACCTGCA CAAAGGCGTG         60

CAGTGGATCC CGCGGGACGG TCACCTGCAC AAAGGCGTGC AGTGGATCCC GCCCCGACGG         120

TCACCTGCAC AAAGGCGTGC AGTGGATCCG ACGGTCACCT GCACAAAGGC GTGCAGTGGA         180

TCCCG                                                                    185
```

(2) INFORMATION FOR SEQ ID NO:4:

(i) SEQUENCE CHARACTERISTICS:
      (A) LENGTH: 162 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:4:

```
GACGGTCACC TGCACAAAGG CGTGCAGTGG ATCCCGGCGG ACGGTCACCT GCACAAAGGC         60

GTGCAGTGGA TCCCGTGACG GTCACCTGCA CAAAGGCGTG CAGTGGATCC CGCCAGACGG         120
```

```
TCACCTGCAC AAAGGCGTGC AGTGGATCCG CCAGACGGTC AC                162
```

(2) INFORMATION FOR SEQ ID NO:5:

(i) SEQUENCE CHARACTERISTICS:
        (A) LENGTH: 280 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:5:

```
GACGGTCACC TGCACAAAGG CGTGCAGTGG ATCCCGCCGG GACGGTCACC TGCACAAAGG    60

CGTGCAGTGG ATCCCGTGAC GGTCACCTGC ACAAAGGCGT GCAGTGGATC CCGGACGGTC   120

ACCTGCACAA AGGCGTGCAG TGGATCCCGC CGGGACGGTC ACCTGCACAA AGGCGTGCAG   180

TGGATCCCGA CGGTCACCTG CACAAAGGCG TGCAGTGGAT CCCGACGGTC ACCTGCACAA   240

AGGCGTGCAG TGGATCCCGC CGGGACGGTC ACCTGCACAA                        280
```

(2) INFORMATION FOR SEQ ID NO:6:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:6:

```
GACGGTCACC TGCACAAAGG CGTGCAGTAG ATCCCGCCCG GACGGTCACC TGCACAAAGG    60

CGTGCAGTGG ATCCCGGACG GTCACCTGCA CAAAGGCGTG CAGTGGATCC CGCGACGGTC   120

ACCTGCACAA AGGCGTGCAG TGGATCCCGC CGGGACGGTC ACCTGCACAA AGGCGTGCAG   180

TGGATCCCGA CGGTCACCTG CACAAAGGCG TGCAGTGGAT CCCGGACGGT CACCTGCACA   240

AAGGCG                                                             246
```

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:7:

```
CGGGATCCAC TGCACGCCTT TG                                            22
```

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:8:

-continued

```
GACGGTCACC TGCACAGGCG                                              20
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:9:

```
CGGGATCCAC TGCACGCCTG A                                            21
```

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:10:

```
GACGGACACC TGCAAACGGA GC                                           22
```

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:11:

```
CGGGATCCAC TGCAGCTCCG TTA                                          23
```

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:12:

```
CTGGGTCACC TGCACAAAGG CG                                           22
```

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:13:

GACCCACACC TGCACAAAGG CG                                              22

(2) INFORMATION FOR SEQ ID NO:14:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:14:

GACGGTGTGC TGCACAAAGG CG                                              22

(2) INFORMATION FOR SEQ ID NO:15:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:15:

GACGGTCACG ACCACAAAGG CG                                              22

(2) INFORMATION FOR SEQ ID NO:16:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:16:

CGGGATCCAC TCGTCGCCTT TGA                                             23

(2) INFORMATION FOR SEQ ID NO:17:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:17:

CGGGATCCTG AGCACGCCTT TGA                                             23

(2) INFORMATION FOR SEQ ID NO:18:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:18:

CGGGAAGGAC TGCACGCCTT TGA                                                    23

(2) INFORMATION FOR SEQ ID NO:19:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:19:

CGCCTTCCAC TGCACGCCTT TGA                                                    23

(2) INFORMATION FOR SEQ ID NO:20:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:20:

GCGGATCCAC TGCACGCCTT TGA                                                    23

(2) INFORMATION FOR SEQ ID NO:21:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:21:

GANGGTCACC NGCACAAAGG CG                                                     22

(2) INFORMATION FOR SEQ ID NO:22:

(i) SEQUENCE CHARACTERISTICS:
            (A) LENGTH: 314 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:22:

GACGGTCGCC GGCACAAAGG CGTGCAGTGG ATCCCGGACG GTCACCCGCA CAAAGGCGTG          60

CAGTGGATCC CGGACGGTCA CCGGCACAAA GGCGTGCAGT GGATCCCGGA CGGTCACCTG         120

CACAAAGGCG TGCAGTGGAT CCCGGATGGT CACCAGCACA AAGGCGTGCA GTGGATCCCG         180

ACGGTCACCC GCACAAAGGC GTGCAGTGGA TCCCGGACGG TCACCTGCAC AAAGGCGTGC         240

AGTGGATCCC GACGGTCACC AGCACAAAGG CGTGCAGTGG ATCCCGGACG GTCACCTGCA         300

CAAAGGCGTG CAGG                                                          314

(2) INFORMATION FOR SEQ ID NO:23:

(i) SEQUENCE CHARACTERISTICS:
        (A) LENGTH: 408 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:23:

```
GACGGTCACC TGCACAAAGG CGTGCAGTGG ATCCCGGACG GTCACCTGCA CAAAGGCGTG      60

CAGTGGATCC CGGACGGTCA CCAGCACAAA GGCGTGCAGT GGATCCCGAC GGTCACCCGC     120

ACAAAGGCGT GCAGTGGATC CCGGATGGTC ACCGGCACAA AGGCGTGCAG TGGATCCCGA     180

CGGTCACCTG CACAAAGGCG TGCAGTGGAT CCCGCGTGAG GGTCACCTGC ACAAAGGCGT     240

GCAGTGGATC CCGACGGTCA CCTGCACAAA GGCGTGCAGT GGATCCCGAC GGTCACCTGC     300

ACAAAGGCGT GCAGTGGATC CCGCCGGGAC GGTCACCTGC ACAAAGGCGT GCAGTGGATC     360

CCGGACGGTC ACCGGCACAA AGGCGTGCAG TGGATCCCGG ACGGTCAC               408
```

(2) INFORMATION FOR SEQ ID NO:24:

(i) SEQUENCE CHARACTERISTICS:
        (A) LENGTH: 674 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:24:

```
GGTCACCGGC ACAAAGGCGT GCAGTGGATC CCGCCGGGAC GGTCACCTGC ACAAAGGCGT      60

GCAGTGGATC CCGCCGGGAC GGTCACCTGC ACAAAGGCGT GCAGTGGATC CCGGACGGTC     120

ACCTGCACAA AGGCGTGCAG TGGATCCCGC CGGGACGGTC ACCTGCACAA AGGCGTGCAG     180

TGGATCCCGG ACGGTCACCT GCACAAAGGC GTGCAGTGGA TCCCGACGGT CACCAGCACA     240

AAGGCGTGCA GTGGATCCCG AAGGTCACCC GCACAAAGGC GTGCAGTGGA TCCCGGACGG     300

TCACCGGCAC AAAGGCGTGC AGTGGATCCC GACGGTCACC TGCACAAAGG CGTGCAGTGG     360

ATCCCGACGG TCACCGGCAC AAAGGCGTGC AGTGGATCCC GCCGGGAAGG TCACCTGCAC     420

AAAGGCGTGC AGTGGATCCC GGACGGTCAC CGGCACAAAG GCGTGCAGTG GATCCCGGAA     480

GGTCACCGGC ACAAAGGCGT GCAGTGGATC CCGACGGTCA CCAGCACAAA GGCGTGCAGT     540

GGATCCCGGA CGGTCACCGG CACAAAGGCG TGCAGTGGAT CCCGGACGGT CACCTGCACA     600

AAGGCGTGCA GTGGATCCCG ACGGTCACCC GCACAAAGGC GTGCAGTGGA TCCCGCCGGG     660

ATGGTCACCG GCAC                                                       674
```

(2) INFORMATION FOR SEQ ID NO:25:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:25:

```
GAGGGTCACC CGCACAAAGG CGTGCACTGG ATCCCGCCGG GACGGTCACC TGCACAAAGG        60

CGTGCATTGG ATCCCGCCGG GACGGTCACC GGCACAAAGG GGTGCAGTGG ATCCCGGACG       120

GTCACCTGCA CAAAGGCGTG CAGTGGATCC CGCCGGGACG GTCACCGGCA CAAAGGCGTG       180

CAGTGGATCC CGATGGTCAC CCGCACAAAG GCGTGCAGTG GATCCCGATG GTCACCCGCA       240

CAAAGGCGTG CAGTGGATCC CGCCGGGACG GTCACCTGCA CAAAGGCGTG CAGTGGATCC       300

CGACGGTCAC CTGCACAAAG GCGTGCAGTG GATCCCGGAA GGTCACCGGC ACAAAGGCGT       360

GCAGTGGATC CCG                                                         373
```

METHOD OF FORMING A MACROMOLECULAR MICROGENE POLYMER

FIELD OF THE INVENTION

The present invention relates to a method of forming a macromolecular microgene polymer by use of DNA polymerase.

BACKGROUND OF THE INVENTION

The advent of evolutional molecular engineering has made it feasible to create an enzyme (protein) forming the basis of life reaction or a gene coding therefor in laboratories. By this technology, an enzyme (protein) with new activity not occurring in nature can be produced and expected for use in various applications to the fields of medicine and engineering.

An enzyme (protein) or a gene coding therefor is composed of a polymer of amino acids or nucleotides as a block unit. In evolutional molecular engineering, a molecule with desired activity is selected from a pool of polymers consisting of random amino acid or nucleotide block units.

However, even if it is attempted to prepare polymers with every combination, there is a limit to the physical amount of compounds which can be synthesized, so there is a limit to the number of blocks which can be linked, and as a consequence, a too large protein or gene cannot be created. Further, in consideration of an in vitro evolutional system for translating a protein from a nucleic acid polymer, the appearance of "termination codon" terminating the translation is a great problem. Therefore, a microgene which is large to a certain extent is preferably used as a block unit to form a gene coding for a large protein.

There is the hypothesis that a large gene was born by repeatedly polymerizing a small gene (microgene) (S. Ohno & J. T. Epplen, Proc. Natl. Acad. Sci. U.S.A. 80:3391–3395). Because it is considered that a polypeptide rich in a simple repeating structure can easily have a stable secondary structure, evolutional molecular engineering directed at large proteins or genes requires the techniques of repeatedly polymerizing a short structural unit to synthesize a macromolecule (Nature 367:323–324, 1994).

At present, a rolling circle synthesis method is reported as a method of preparing a polymer consisting of a short repeating DNA unit (PNAS 92:4641–4645, 1995).

However, this method should go through a plurality of steps including phosphorylation reaction, linkage reaction, polymerization reaction, double-stranded chain forming reaction, so its complicated reaction system is problematic.

Under these circumstances, there have been demands for developments in a reaction system in which a gene polymer can be formed more simply.

SUMMARY OF THE INVENTION

The object of the present invention is to provide a method of efficiently and simply forming a polymer consisting of a repeating microgene.

As a result of their extensive research, the present inventors found that a macromolecular microgene polymer can be formed efficiently and simply by allowing DNA polymerase to act on oligonucleotides complementary at least partially to each other, to complete the present invention.

That is, the present invention is a method of forming a macromolecular microgene polymer, which comprises allowing DNA polymerase to act on oligonucleotides A and B complementary at least partially to each other to effect polymerase chain reaction (PCR).

The DNA polymerase includes exonucleases, particularly those acting in the 3'→5' direction. In addition, the DNA polymerase is preferably thermally stable.

In the method of forming a macromolecular microgene polymer according to the present invention, the 3-terminals of oligonucleotide A and/or oligonucleotide B can contain at least one nucleotide not capable of forming a base pair with the other oligonucleotide.

BRIEF DESCRIPTION OF THE DRAWINGS

FIG. 3 shows genes synthesized by the method of the present invention.

FIG. 8 is a photograph showing the result of agarose gel electrophoresis.

FIG. 9 shows genes synthesized by the method of the present invention.

DETAILED DESCRIPTION OF THE INVENTION

Hereinafter, the present invention is described in detail.

Figure 1:
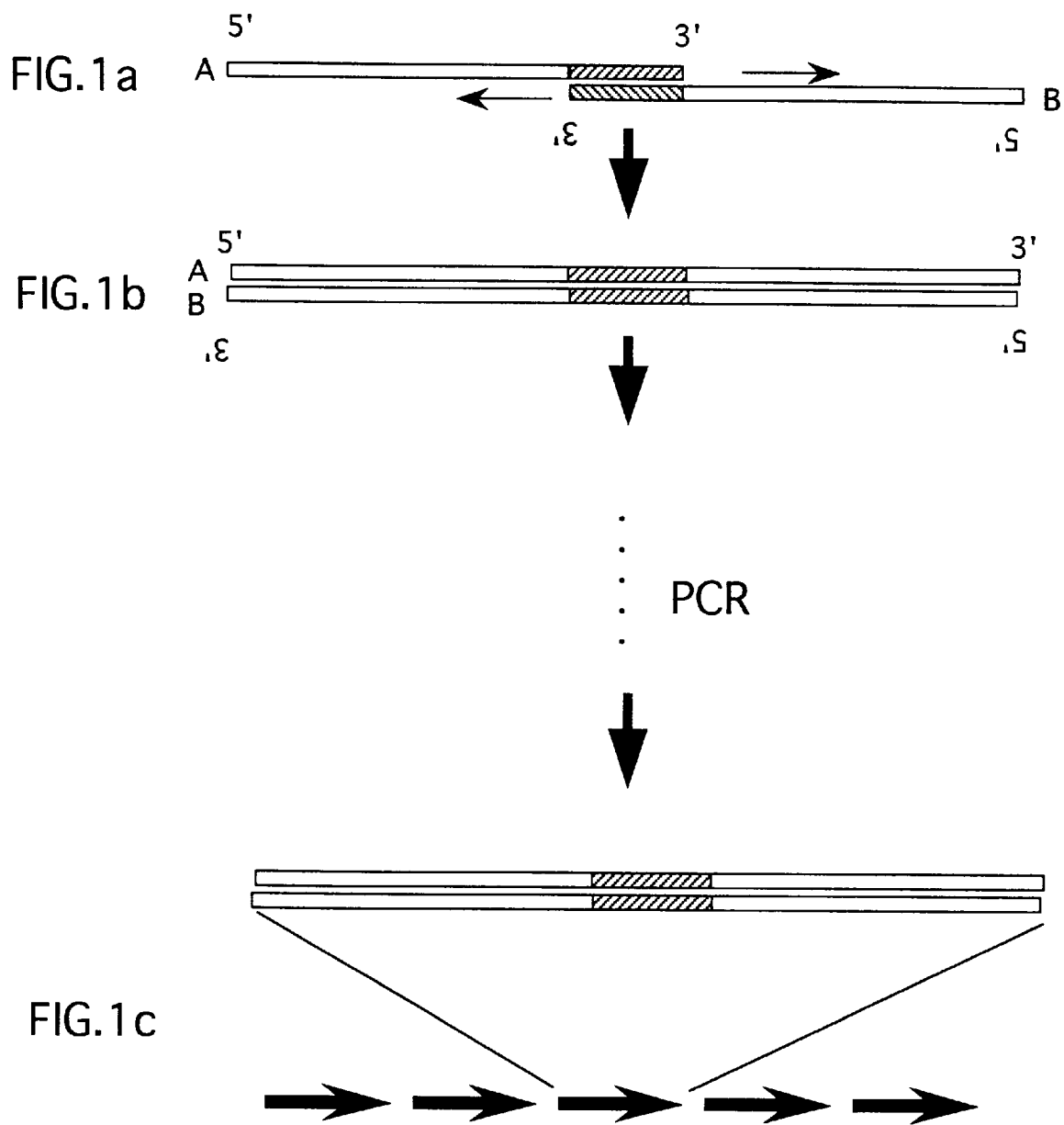
FIG. 1a to FIG. 1c is a schematic drawing showing the method of the present invention.

As shown in FIG. 1a, two oligonucleotides (oligonucleotides A and B) with complementary regions being at least partially to each other are synthesized before conducting polymerase chain reaction according to the present invention. In the present invention, oligonucleotides A and B are synthesized so as to be complementary to each other particularly in their 3'-terminal sequences. The number of oligonucleotides forming a complementary chain to each other is preferably at least 6, more preferably at least 8, although there is no particular limitation.

Alternatively, oligonucleotides A and B may be synthesized such that the 3-terminals of oligonucleotide A and/or oligonucleotide B contain 1 or more nucleotides (preferably 1 to 3 nucleotides) being not capable of forming base pairs with the other oligonucleotide. By this operation, the efficiency of reaction can be raised.

Further, because one object of the present invention is to create a completely new gene polymer not occurring in the nature, said 2 oligonucleotides are not particularly limited and may be selected arbitrarily insofar as they are at least partially complementary to each other. The synthesized oligonucleotides form a double-stranded chain in only the part of their complementary region.

As used herein, the term "complementary" can refer not only to the relationship between adenine and thymidine or guanine and cytosine, but also to the relationship between guanine and thymine or the like insofar as oligonucleotides A and B are at least partially complementary to each other.

Oligonucleotides A and B function as primers to initiate PCR at their complementary region (a double-stranded chain in FIG. 1a), where the single-stranded chain (i.e. not forming the double-stranded chain with oligonucleotide B) of oligonucleotide A acts as a template for synthesizing oligonucleotide B and the single-stranded chain (i.e. not forming the double-stranded chain with oligonucleotide A) of oligonucleotide B acts as a template for synthesizing oligonucleotide A (FIG. 1a). If PCR is conducted by allowing e.g. thermostable DNA polymerase with the 3'→5' exonuclease activity to act on said 2 oligonucleotides, double-stranded DNA is synthesized as a repeating unit (FIG. 1b). By further continuing the PCR, large DNA consisting of continuous repeating units is synthesized (FIG. 1c).

The PCR using polymerase (e.g. Taq polymerase) is carried out by conducting 1 cycle at 94° C. for 10 to 120 seconds, 30 to 65 cycles each at 69° C. for 10 to 120 seconds, and 1 cycle at 69° C. for 3 to 7 minutes.

To conduct PCR efficiently, additional reaction at 94° C. for 10 minutes and at 69° C. for 10 minutes is preferably carried out before conducting the above cycles.

In this manner, the complementary part of the 2 oligonucleotides serves as a self-primer and the other oligonucleotide serves as a template for synthesizing them, resulting in polymerization of DNA with double-stranded chain DNA as a repeating unit (FIG. 1b) with an extremely large number of copies in the same direction (FIG. 1c). In the present invention, the replacement, insertion and/or deletion of several nucleotides may occur between repeating units insofar as the repeating units form a complementary chain.

EXAMPLES

Hereinafter, the present invention is described in more detail by reference to Examples which however are not intended to limit the scope of the present invention.

Example 1

KY-794 (SEQ ID NO:1) and KY-795 (SEQ ID NO:2) were synthesized respectively as oligonucleotides A and B for use in PCR. The synthesized oligonucleotides A and B were composed of 22 and 23 nucleotides respectively where their 3'-terminal 8 nucleotides were complementary to each other (the sequence at the 15- to 22-positions in KY-794 was complementary to the sequence at the 15- to 22-positions in KY-795). Adenine (A) was added to the 3'-terminal of KY-795 to prevent formation of a base pair with KY-794.

The conditions for PCR using the above oligonucleotides in a 50 µl reaction volume are as follows:

| | |
|---|---|
| KY-794 (SEQ ID NO: 1) | 20 pmol |
| KY-795 (SEQ ID NO: 2) | 20 pmol |
| dNTP | 350 µM |
| MgCl$_2$ | 1.75 mM |
| Tris-HCl, pH 9.2 | 50 mM |
| (NH$_4$)$_2$SO$_4$ | 14 mM |
| Taq polymerase | 2.6 units/50 µl |

The Taq polymerase used was a mixture of Taq polymerase and Pwo polymerase contained in Expand™ Long Template PCR system (Boehringer).

PCR was carried out using 9600 or 2400 PCR system (Perkin Elmer) for cycle reaction under the following conditions:

| | |
|---|---|
| 94° C. | 10 minutes |
| 69° C. | 10 minutes |
| (94° C. for 10 seconds and 69° C. for 60 seconds) × 45 cycles | |
| 69° C. | 7 minutes |

The enzyme was added when the system reached 94° C.

The PCR product obtained under these conditions was subjected to 1.2% agarose gel electrophoresis.

Figure 2:
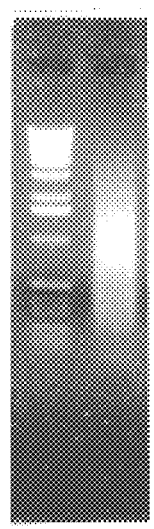
FIG. 2 is a photograph showing the result of agarose gel electrophoresis.

The result is shown in FIG. 2.

As can be seen from FIG. 2, DNA reaching several kilo base pairs or more can be polymerized in this method.

The polymer thus obtained was cloned into plasmid vector pTZ19R (Mead et al., Protein Eng. 1:67–74 (1986)). For 4 clones (pSA32, pSA33, pYT5 and pYT8), their insert fragments were sequenced using a sequencer (Perkin Elmer).

The results are shown in FIG. 3. The nucleotide sequences determined for the respective clones are shown in SEQ ID NO: 3 for pSA32, SEQ ID NO: 4 for pSA33, SEQ ID NO: 5 for pYT5, and SEQ ID NO: 6 for pYT8.

In SEQ ID NO:3, the sequences at the 1- to 36-positions, the 40- to 75-positions and the 77- to 112-positions are identical with one another, so it is understood that a polymer was synthesized in which many of double-stranded chains as repeating units each consisting of 37 base pairs derived from KY-794 and KY-795 had been linked in the same direction. This applies to SEQ ID NOS:4–6.

In FIG. 3, "Δ" indicates the absence of the corresponding nucleotide in the linking region of the repeating units each consisting of the sequence derived from the oligonucleotides, and the underlined nucleotides are an insert of unknown origin in the linking region of the repeating units.

Example 2

In the reaction shown in Example 1 (FIG. 2), the 3'-terminal of KY795 had one nucleotide being not capable of forming a base pair with KY-794. In this example, polymerization was carried out using the combination of oligonucleotide KY-783 (SEQ ID NO:7) and oligonucleotide KY-794, i.e. the combination not forming such a mismatch.

The conditions for PCR were identical to those in Example 1. The PCR product obtained under these conditions was subjected to 1.2% agarose gel electrophoresis.

Figure 4:
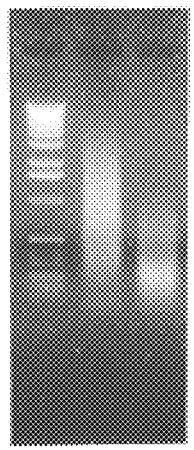
FIG. 4 is a photograph showing the result of agarose gel electrophoresis.

The result is shown in FIG. 4.

As can be seen from FIG. 4, the efficiency of polymerization is improved when at least one nucleotide being not capable of forming a base pair with the other oligonucleotide is present at the 3'-terminal of the oligonucleotide (FIG. 4, lane 2).

Example 3

Figure 5:
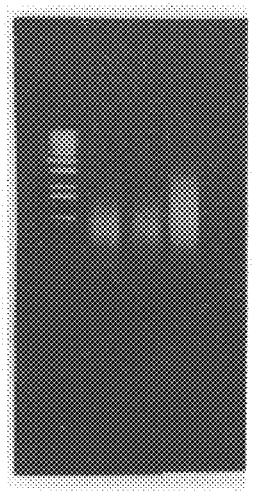
FIG. 5 is a photograph showing the result of agarose gel electrophoresis.

As shown in FIG. 5, KY-794 and KY-795 have a complementary region of 8 bases. In this example, polymerization was carried out using oligonucleotide KY-845 (SEQ ID NO:8) and oligonucleotide KY-846 (SEQ ID NO:9) whose complementary region consisted of 6 nucleotides which is shorter by 2 bases than above. The composition of the reaction solution was the same as in Example 2 except that PCR was carried out under the following cycle conditions 1 or 2:

| (Conditions 1) | |
| --- | --- |
| 94° C. | 10 minutes |
| 63° C. | 10 minutes |
| (94° C. for 10 seconds and 63° C. for 60 seconds) × 45 cycles | |
| 63° C. | 7 minutes; |
| (Conditions 2) | |
| 94° C. | 10 minutes |
| 66° C. | 10 minutes |
| (94° C. for 10 seconds and 66° C. for 60 seconds) × 45 cycles | |
| 66° C. | 7 minutes |

The PCR products obtained under these conditions were subjected to 1.2% agarose electrophoresis.

The results are shown in FIG. 5.

In FIG. 5, lanes 2 and 3 were obtained under Conditions 1 and lanes 4 and 5 under Conditions 2.

As can be seen from lanes 1 and 2 in FIG. 5, the polymerization reaction proceeds by decreasing the annealing temperature of the PCR cycle to 63° C. even by the combination of the oligonucleotides having a complementary region of as short as 6 bases.

Example 4

In this example, thermostable DNA polymerase having the 3'→5' exonuclease activity was used as an enzyme for PCR. The 3'→5' exonuclease activity is important for raising polymerization efficiency. Accordingly, the importance of the 3'→5' exonuclease activity was examined using thermostable DNA polymerase lacking in the 3'→5' exonuclease activity.

The oligonucleotides used were KY-794 (SEQ ID NO:1) and KY-795 (SEQ ID NO:2). The PCR reaction solution had the same composition as in Example 1 except that the enzyme was 1.9 units/50 μl of thermostable polymerase Pfu DNA polymerase commercially available from Stratagene or Exo-Pfu DNA polymerase assumed to lack the 3'→5' exonuclease activity. PCR was carried out under the same cycle conditions as in Example 1. The PCR product obtained under these conditions was subjected to 2% agarose gel electrophoresis.

Figure 6:
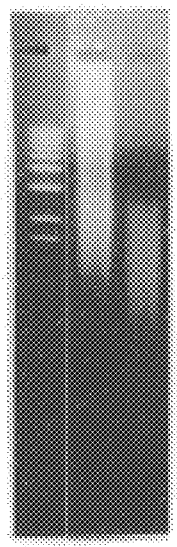
FIG. 6 is a photograph showing the result of agarose gel electrophoresis.

The result is shown in FIG. 6.

As can be seen from FIG. 6, polymerization efficiency was dropped where Exo-Pfu DNA polymerase assumed to lack the 3'→5' exonuclease activity was used(lane 3) as compared with the case where Pfu DNA polymerase having the 3'→5' exonuclease activity was used (lane 2).

Example 5

In this example, polymerization was carried out using oligonucleotides with various sequences.

Figure 7:
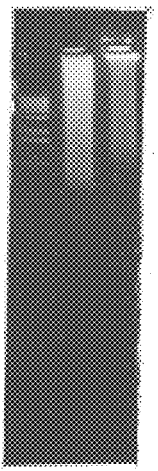
FIG. 7 is a photograph showing the result of agarose gel electrophoresis.

As shown in FIG. 7, the combination of KY-794 (SEQ ID NO:1) and KY-795 (SEQ ID NO:2) and the combination of KY-808 (SEQ ID NO:10) and KY-809 (SEQ ID NO:11) are identical in the number (=8) of nucleotides forming a complementary chain, but are greatly different in the nucleotide composition of the complementary region. KY-827 (SEQ ID NO:12), KY-828 (SEQ ID NO:13), KY-829 (SEQ ID NO:14) and KY-830 (SEQ ID NO:15) are partially modified sequences of KY-794 (SEQ ID NO:1), and KY-831 (SEQ ID NO:16), KY-832 (SEQ ID NO:17), KY-833 (SEQ ID NO:18), KY-834 (SEQ ID NO:19) and KY-835 (SEQ ID NO:20) are partially modified sequences of KY-795 (SEQ ID NO:2).

PCR was carried out under the same conditions as in Example 1 by using each of the following combinations: KY-794 (SEQ ID NO:1) and KY-795 (SEQ ID NO:2); KY-808 (SEQ ID NO:10) and KY-809 (SEQ ID NO:11); KY-827 (SEQ ID NO:12) and KY-795 (SEQ ID NO:2); KY-828 (SEQ ID NO:13) and KY-795 (SEQ ID NO:2); KY-829 (SEQ ID NO:14) and KY-795 (SEQ ID NO:2); KY-830 (SEQ ID NO:15) and KY-795 (SEQ ID NO:2); KY-794 (SEQ ID NO:1) and KY-831 (SEQ ID NO:16); KY-794 (SEQ ID NO:1) and KY-832 (SEQ ID NO:17); KY-794 (SEQ ID NO:1) and KY-833 (SEQ ID NO:18); KY-794 (SEQ ID NO:1) and KY-834 (SEQ ID NO:19); and KY-794 (SEQ ID NO:1) and KY-835 (SEQ ID NO:20). The PCR products obtained under these conditions were subjected to 2% agarose gel electrophoresis.

The results are shown in FIGS. 7 and 8.

As can be seen from FIGS. 7 and 8, there are differences in efficiency but the polymerization reaction proceeds in any of the combinations of oligonucleotide sequences used.

Example 6

In order to allow the sequence of the resulting polymer to have diversity, polymerization was carried out using a partially randomized oligonucleotide. KY-812 (SEQ ID NO:21) and KY-795 (SEQ ID NO:2) were used as as primers. KY-812 (SEQ ID NO:21) is an oligonucleotide synthesized such that A, T, G or C is located at the 3- and 11-positions. The PCR reaction was carried out in the same manner as in Example 1. After the reaction, the resulting polymer was cloned into plasmid vector pTZ19R. For 4 clones (pYT15, pYT16, pYT20 and pYT21), their insert fragments were sequenced.

The results are shown in FIG. 9. The nucleotide sequences determined for the respective clones are shown in SEQ ID NO:22 for pYT15, SEQ ID NO:23 for pYT16, SEQ ID NO:24 for pYT20 and SEQ ID NO: 25 for pYT22.

As can be seen from FIG. 9, the base at the 3-position had a preference for C, while A, T, G or C appeared as the base at the 11-position, so diversity was given to the sequence of the polymer.

Example 7

The protein encoded by the resulting polymer can be expressed in *E. coli*. The polymer obtained by the combination of KY-794 (SEQ ID NO:1) and KY-795 (SEQ ID NO:2) and the polymer obtained by the combination of KY-812 (SEQ ID NO:21) and KY-795 (SEQ ID NO:2) were cloned respectively into expression vector pET23b to give recombinants pYT32 and pYT33. The proteins derived from the polymers encoded by pYT32 and pYT33 were expressed in *E. coli* BL21 (DE3) and their cell extract was analyzed by SDS polyacrylamide gel electrophoresis on 15–25% gradient gel.

Figure 10:
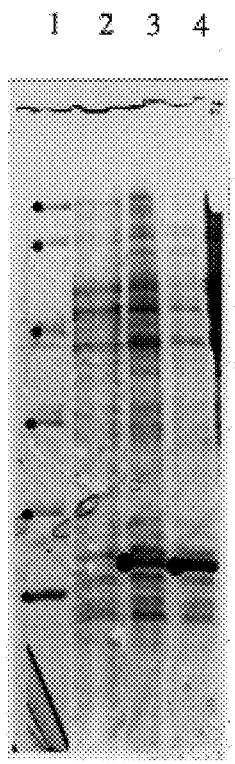
FIG. 10 is a photograph showing the result of SDS polyacrylamide gel electrophoresis.

The results are shown in FIG. 10. The molecular markers are of 97,400, 66,267, 42,400, 30,000, 20,100 and 14,000.

As can be seen from FIG. 10, proteins with a molecular weight of about 16 kDa derived from the polymers are expressed.

As illustrated above, a polymer consisting of a repeating microgene can be formed efficiently and simply according to the present invention.

What is claimed is:

1. A method for forming a double-stranded DNA polymer having repeating subunits in tandem, which comprises:
   a) forming a first mixture comprising a DNA polymerase and two oligonucleotides, wherein the two oligonucleotides have complementary sequences to each other at the 3'-terminal region of each oligonucleotide, and wherein at least one of the oligonucleotides has one to three mismatched, overhanging nucleotides at its 3' terminus;
   b) heating and cooling the first mixture under conditions sufficient to allow for annealing of the two oligonucleotides to each other and extension of the oligonucleotides by the DNA polymerase to form a double-stranded DNA polymer, thereby forming a second mixture containing said double-stranded DNA polymer; and
   c) repeatedly heating and cooling the second mixture to form a double-stranded DNA polymer having repeating units in tandem.

2. The method of claim 1, wherein the DNA polymerase has 3'→5' exonuclease activity.

3. The method of claim 1, wherein the DNA polymerase is thermally stable.

4. The method of claim 1, wherein the complementary sequences at the 3'-terminal region of each oligonucleotide are at least 6 nucleotides in length.

5. A method of producing a protein encoded by a double-stranded DNA polymer having repeating subunits in tandem, which comprises:
   a) forming a first mixture comprising a DNA polymerase and two oligonucleotides, wherein the two oligonucleotides have complementary sequences to each other at the 3'-terminal region of each oligonucleotide, and wherein at least one of the oligonucleotides has one to three mismatched, overhanging nucleotides at its 3' terminus;
   b) heating and cooling the first mixture under conditions sufficient to allow for annealing of the two oligonucleotides to each other and extension of the oligonucleotides by the DNA polymerase to form a double-stranded DNA polymer, thereby forming a second mixture containing said double-stranded DNA polymer;
   c) repeatedly heating and cooling the second mixture to form a double-stranded DNA polymer having repeating units in tandem;
   d) cloning the double-stranded DNA polymer having repeating subunits in tandem into a plasmid vector;
   e) transforming the vector into an organism;
   f) expressing the double-stranded DNA polymer having repeating subunits in tandem in the organism; and
   g) recovering the protein from the organism.

* * * * *